(12) United States Patent
Tran-Thi et al.

(10) Patent No.: US 7,892,851 B2
(45) Date of Patent: Feb. 22, 2011

(54) POROUS HYBRID ORGANIC-INORGANIC MATERIALS FOR THE DETECTION OF HALOGENS

(75) Inventors: Thu-Hoa Tran-Thi, St Fargeau Ponthierry (FR); Clement Sanchez, Bures (FR); Lionel Nicole, Saint Jean du Gard (FR); Peter Hesemann, Montpellier (FR)

(73) Assignees: Commissariat a l'Energie Atomique, Paris (FR); Centre National de la Recherche, Paris (FR); Universite Pierre et Marie Curie (Paris VI), Paris (FR)

( * ) Notice: Subject to any disclaimer, the term of this patent is extended or adjusted under 35 U.S.C. 154(b) by 1096 days.

(21) Appl. No.: 11/547,798

(22) PCT Filed: Apr. 15, 2005

(86) PCT No.: PCT/FR2005/050248
§ 371 (c)(1),
(2), (4) Date: Oct. 6, 2006

(87) PCT Pub. No.: WO2005/100371
PCT Pub. Date: Oct. 27, 2005

(65) Prior Publication Data
US 2007/0214867 A1    Sep. 20, 2007

(30) Foreign Application Priority Data
Apr. 19, 2004    (FR) .................................. 04 04102

(51) Int. Cl.
*G01N 21/76*    (2006.01)
*G01N 21/62*    (2006.01)

(52) U.S. Cl. ........................... 436/172; 422/50; 422/58; 422/83; 436/43; 436/124; 436/164; 436/165

(58) Field of Classification Search ................... 422/55, 422/58, 83; 436/124, 164, 165, 172
See application file for complete search history.

(56) References Cited

U.S. PATENT DOCUMENTS 7,452,845 B2 * 11/2008 Corriu et al. ................. 502/400
7,517,512 B2 *  4/2009 Corriu et al. ................. 423/219
2006/0051826 A1  3/2006 Tran-Thi et al.

FOREIGN PATENT DOCUMENTS

JP    5-230071    9/1993
JP    10-45768    2/1998

* cited by examiner

*Primary Examiner*—Brian J Sines
(74) *Attorney, Agent, or Firm*—Oblon, Spivak, McClelland, Maier & Neustadt, L.L.P.

(57) ABSTRACT

The present invention relates to compounds which can go to make up mesostructured porous hybrid organic-inorganic materials (MPHOIMs) and can serve, within these materials, as probe molecules for the detection or quantitative determination of halogenated gaseous compounds. It also relates to MPHOIMs in which these compounds are grafted by covalent or iono-covalent bonding, to a process for manufacturing these MPHOIMs, and also to chemical sensors for the detection or quantitative determination of halogenated gaseous compounds and comprising these MPHOIMs as sensitive materials.

The invention applies, in particular, to the detection and quantitative determination of halogenated gaseous compounds used in the microelectronics field and, more especially, halogenated boron complexes.

25 Claims, 2 Drawing Sheets

POROUS HYBRID ORGANIC-INORGANIC MATERIALS FOR THE DETECTION OF HALOGENS

TECHNICAL FIELD

The present invention relates to compounds which can go to make up mesostructured porous hybrid organic-inorganic materials (hereinafter MPHOIMs) and can serve, within these materials, as probe molecules for the detection or quantitative determination of halogenated gaseous compounds.

It also relates to MPHOIMs in which these compounds are grafted by covalent or iono-covalent bonding, to a process for manufacturing these MPHOIMs, and also to sensors for the detection or quantitative determination of halogenated gaseous compounds and comprising these MPHOIMs as sensitive materials.

The invention applies, in particular, to the detection and quantitative determination of halogenated gaseous compounds used in the microelectronics field and, more especially, halogenated boron complexes such as, for example, boron trifluoride ($BF_3$) and its derivatives (ether, dihydrate, acetonitrile, etc.) and boron trichloride ($BCl_3$).

It is therefore of most particular interest for the monitoring and control of any possible pollution of the atmosphere or of more or less confined atmospheres, with halogenated gaseous compounds of this type, and in particular for the monitoring of industrial sites which manufacture the latter, and/or which store them and/or use them.

PRIOR ART

Since the discovery by Beck et al. in 1992, mesoporous materials with structuring surfactants, which are most commonly referred to by the acronym MTS or, more generally, by the acronym MPHOIMs, have attracted the interest of a large number of laboratories due to their very specific structures.

Specifically, these materials, which are obtained by polycondensing, according to the sol-gel process, networks of metal oxides (typically derived from silicon alkoxides) in the presence of a surfactant, the molecules of which form organized micelles on a nanometre scale, and then eliminating the surfactant micelles, have the particularity of exhibiting a periodically organized porosity.

Thus, the polycondensation of the metal oxide networks around the micelles of the surfactant results in the formation of a periodically organized hybrid organic-inorganic phase; then, the elimination of the surfactant phase frees the porosity. It is the inorganic replica of the organized micelle phase which confers on the material a periodic structure, for example of cubic, hexagonal or lamellar type.

This structure can be controlled, just as the diameter of the pores can be adjusted during the synthesis of the MPHOIMs. It is in particular possible to vary the pore diameter by adjusting the surfactant chain length or by using a swelling agent, generally a hydrocarbon, which will become solubilized in the surfactant micelles so as to increase the volume thereof.

This possibility of adjusting the pores of the MPHOIMs means that the latter are particularly advantageous for use as sensitive materials in sensors for detecting and quantifying molecular species, since it can be taken advantage of for promoting the penetration and the diffusion, in the sensor, of the molecular species that it is desired to sense.

However, the use of MPHOIMs as sensitive materials of chemical or biological sensors means that there must be present, in the pores of these materials, probe molecules which are accessible and are suitable for the compounds that it is desired to sense, i.e. molecules which are capable of interacting specifically with these compounds and of revealing the presence thereof and, optionally, the concentration in a complex mixture through the emission of a detectable signal.

The aim of the invention is, precisely, to provide compounds which are both capable of being grafted in an MPHOIM by covalent or iono-covalent bonding and capable of being used, within this material, as probe molecules for the detection and quantitative determination of halogenated gaseous compounds, and in particular of halogenated boron complexes.

The aim of the present invention is also to provide MPHOIMs in which these compounds are grafted by covalent or iono-covalent bonding, and also sensors for the detection or quantitative determination of halogenated gaseous compounds and comprising such MPHOIMs as sensitive materials.

Patent applications JP No. 10-045768, EP No. 1 205 177 and JP No. 5-230071, describe diphenyl β-diketones in which one of the phenyl groups is substituted either with an —$O(CH_2)_3$—$Si(OC_2H_5)_2CH_3$ group (JP-A-10-045768), or with an —$O(CH_2)_3$—$Si(OC_2H_5)_3$ group (EP-A-1 205 177), or else an —$O(CH_2)_3$—$SiR_q(R')_{3-q}$ group where q is from 0 to 3, R is an alkoxy, cycloalkoxy or aryloxy group, and R' is a monovalent hydrocarbon group (JP-A-5-230071).

The diphenyl β-diketones described in JP-A-10-045768 and JP-A-5-230071 are intended to be used as UV-absorbers in mainly cosmetic compositions, whereas that described in EP-A-1 205 177 is proposed as an intermediate product for obtaining a conjugate which can be used in dermatological or cosmetic compositions.

The use of these β-diketones as probe molecules, in particular in MPHOIMs, is in no way envisaged in these documents.

DISCLOSURE OF THE INVENTION

A subject of the invention is therefore, firstly, a compound corresponding to at least one of the general formulae (I) and (II) below:

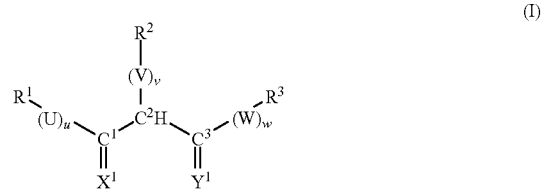

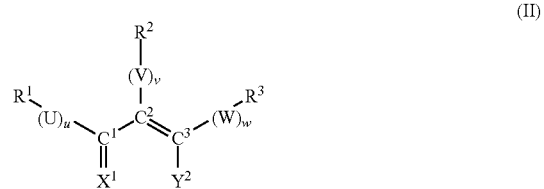

in which:

$X^1$ and $Y^1$ represent, independently of one another, an oxygen or sulphur atom or an =NH group;

$Y^2$ represents an —OH, —SH or —$NH_2$ group;

u, v and w are, independently of one another, 0 or 1, with the proviso, however, that at least one of u, v and w is other than 0;

U, V and W represent, independently of one another, an aryl or heteroaryl group having one or more rings, each having 5 or 6 ring members;

at least one of $R^1$, $R^2$ and $R^3$ represents a group —$(Z)_z K$ in which:

z is 0 or 1, Z represents a $C_3$ to $C_6$ cyclic, or $C_1$ to $C_6$ linear or branched, saturated or unsaturated divalent hydrocarbon group, this hydrocarbon group optionally containing one or more oxygen, nitrogen or sulphur atoms; and K represents:

either a group —$Si(Cl)_m(OR^4)_n(R^5)_p$ in which:

m and n are integers ranging from 0 to 3, p is an integer ranging from 0 to 2, with the proviso, however, that m+n is equal to 1, 2 or 3 and m+n+p is equal to 3;

$R^4$ and $R^5$ represent, independently of one another, a $C_3$ to $C_6$ cyclic, or $C_1$ to $C_6$ linear or branched, saturated or unsaturated hydrocarbon group, this hydrocarbon group optionally containing one or more oxygen, nitrogen or sulphur atoms, or else an aryl or heteroaryl group having a 5- or 6-membered ring;

or a metal-complexing group;

and in which that or those of $R^1$, $R^2$ and $R^3$ which does not or do not represent a group —$(Z)_z K$, if there is one, represent(s) a hydrogen or halogen atom, a —CN or —$NO_2$ group, a $C_3$ to $C_6$ cyclic, or $C_1$ to $C_6$ linear or branched, saturated or unsaturated hydrocarbon group, this hydrocarbon group optionally containing one or more oxygen, nitrogen or sulphur atoms, or else an aryl or heteroaryl group having a 5- or 6-membered ring;

with the exclusion of compounds in which one of $R^1$ and $R^3$ represents is other than a group —$O(CH_2)_3$—$Si(OR^4)_n(R^5)_p$ when U and W both represent a phenyl group, v is 0, $R^2$ represents a hydrogen atom, $X^1$ and $Y^1$ both represent an oxygen atom or $X^1$ represents an oxygen atom and $Y^2$ represents an —OH group.

Thus, the compound according to the invention has the characteristics of comprising:

firstly, a functional group which is capable of reacting with a halogenated gaseous compound and of forming with the latter a complex, which corresponds to the assembly $X^1=C^1-C^2H-C^3=Y^1$ in general formula (I) and to the assembly $X^1=C^1-C^2=C^3-Y^2$ in general formula (II) and which is conjugated to at least one aryl or heteroaryl group, represented by U, V and/or W, in such a way that the complex formed is fluorescent and therefore detectable by fluorimetry or by absorption spectroscopy; and secondly, at least one functional group which allows the grafting, by covalent or iono-covalent bonding, of the compound in an MPHOIM and which corresponds to the letter K of the group —$(Z)_z K$ constituting at least one of $R^1$, $R^2$ and $R^3$.

It should be noted that general formulae (I) and (II) encompass compounds which can, depending on the medium in which they find themselves, be either in a single form corresponding to one of these formulae, or in two tautomeric forms in equilibrium, corresponding, respectively, to the two general formulae (I) and (II) in which U, V, W, u, v, w, $R^1$, $R^2$, $R^3$ and $X^1$ are identical from one formula to the other.

Thus, for example, β-diketones, i.e. the compounds of general formula (I) in which $X^1$ and $Y^1$ both represent an oxygen atom, can be in equilibrium with their enol form, corresponding to general formula (II) in which $X^1$ represents an oxygen atom and $Y^2$ represents an —OH group.

Similarly, β-thiooxoketones, i.e. the compounds of general formula (I) in which $Y^1$ represents an oxygen atom when $X^1$ represents a sulphur atom, and $Y^1$ represents a sulphur atom when $X^1$ represents an oxygen atom, can be in tautomeric equilibrium with their enol-enethiol forms corresponding to general formula (II) in which $Y^2$ represents an —OH group when $X^1$ represents a sulphur atom (enol), and $Y^2$ represents an —SH group when $X^1$ represents an oxygen atom (enethiol).

It is for this reason that, in the above text and subsequent text, the compound according to the invention is considered to be able to correspond to at least one of general formulae (I) and (II).

In the context of the invention, a $C_1$ to $C_6$ linear or branched, saturated or unsaturated hydrocarbon group can be any alkyl, alkenyl or alkynyl group containing from 1 to 6 carbon atoms, such as, for example, a methyl, ethyl, propyl, isopropyl, butyl, pentyl, neopentyl, hexyl, ethylenyl, propylenyl, butenyl, pentenyl, hexenyl, methylpentenyl, buta-1,3-dienyl, ethynyl, propynyl, butynyl, pentynyl or hexynyl group. Preferably, this hydrocarbon group is a $C_1$ to $C_3$ alkyl group or a $C_2$ or $C_3$ alkenyl group.

A $C_3$ to $C_6$ cyclic, saturated or unsaturated hydrocarbon group can be any cycloalkyl or cycloalkenyl group containing from 3 to 6 carbon atoms, such as, for example, a cyclopropyl, cyclobutyl, cyclopentyl, cyclohexyl, cyclopropenyl, cyclobutenyl, cyclopentenyl or cyclohexenyl group. When this cyclic hydrocarbon group contains one or more oxygen, nitrogen or sulphur atoms, it can in particular be a tetrahydrofuryl, tetrahydrothiophenyl, pyrrolidinyl, piperidinyl or dioxanyl group.

An aryl or heteroaryl group having one or more rings, each having 5 or 6 ring members, can be any group consisting of a single ring comprising 5 or 6 atoms chosen from carbon, oxygen, nitrogen and sulphur and containing at least two conjugated double bonds, or of several rings of this type attached to one another. By way of examples of aryl and heteroaryl groups having a single 5- or 6-membered ring, mention may be made of cyclopentadienyl, phenyl, benzyl, furyl, pyrrolyl, thiophenyl, oxazolyl, isoxazolyl, thiazolyl, isothiazolyl, imidazolyl, triazolyl, pyridinyl, pyranyl, pyrazinyl and pyrimidinyl groups, while, by way of examples of aryl or heteroaryl groups having several rings, each having 5 or 6 ring members, mention may be made of biphenyl, phenylacetylenyl, pyrene, anthracene, indolyl, pteridinyl, quinolyl and isoquinolyl groups.

Moreover, in general formulae (I) and (II), when u is 0, U is absent and $R^1$ is attached via a single bond to the carbon atom $C^1$; when v is 0, V is absent and $R^2$ is attached via a single bond to the carbon atom $C^2$, while, when w is 0, W is absent and $R^3$ is attached via a single bond to the carbon atom $C^3$.

Similarly, when z is equal to 0, Z is absent and K is attached via a single bond to U, V and/or W according to the meaning of $R^1$, $R^2$ and $R^3$, or to the carbon atoms $C^1$, $C^2$ and/or $C^3$ according to the meaning of u, v and w.

According to a preferred arrangement of the compound according to the invention, the latter is a β-diketone, optionally in equilibrium with its enol form, such β-diketones forming, in fact, with the halogenated gaseous compounds, and in particular with halogenated boron complexes such as $BF_3$, complexes whose fluorescence is both enhanced and shifted to longer wavelengths (this is referred to as a batochrome shift).

According to another preferred arrangement of the compound according to the invention, the latter corresponds to at least one of general formulae (I) and (II) in which:

either v is 0, while u and w are 1, in which case U and W both represent an aryl or heteroaryl group having one or more rings, each having 5 or 6 ring members, and $X^1$, $Y^1$, $Y^2$, $R^1$, $R^2$ and $R^3$ are as defined above;

or u and v are 0, while w is 1, in which case only W represents an aryl or heteroaryl group having one or more 5- or 6-membered rings, and $X^1$, $Y^1$, $Y^2$, $R^1$, $R^2$ and $R^3$ are as defined above.

In accordance with the invention, the functional group that the compound according to the invention at least contains for grafting of the latter in an MPHOIM by covalent or iono-covalent bonding, and which corresponds to the letter K of the group $—(Z)_z K$ constituting at least one of $R^1$, $R^2$ and $R^3$, is chosen according to the metal oxide(s) envisaged for forming the inorganic phase of the MPHOIM.

In the context of the present invention, the terms "metal" and "metallic" refer to elements conventionally considered to be metals in the periodic table of elements, in particular the transition elements (such as, for example, titanium, zirconium, niobium, yttrium, vanadium, chromium, cobalt and molybdenum), the other metals (such as aluminium, gallium, germanium and tin), lanthanides and actinides, but also metalloids such as silicon, arsenic and selenium.

Thus, if the MPHOIM in which the compound must be grafted is designed to be based on silicon oxide or aluminium oxide, then K represents a group $—Si(Cl)_m(OR^4)_n(R^5)_p$ where m and n are integers ranging from 0 to 3, p is an integer ranging from 0 to 2, m+n is equal to 1, 2 or 3, m+n+p is equal to 3, and $R^4$ and $R^5$ are as defined above.

In this case, K is preferably chosen from trichlorosilyl $—SiCl_3$, dichloroalkoxysilyl $—SiCl_2(OR^4)$, chlorodialkoxysilyl $—SiCl(OR^4)_2$ and trialkoxysilyl $—Si(OR^4)_3$ groups where $R^4$ is a $C_1$ to $C_6$, preferably $C_1$ to $C_3$, alkyl group, and better still an ethyl group.

As a variant, if the MPHOIM in which the compound must be grafted is designed to be based on an oxide other than silicon oxide, such as, for example, a titanium oxide, aluminium oxide, zirconium oxide, niobium oxide, vanadium oxide, yttrium oxide or cerium oxide, then K represents a metal-complexing group.

In the above text and subsequent text, the expression "metal-complexing group" is intended to mean any polydentate or chelating group having several functions chosen from —OH, —COOH, —NH$_2$, =NOH, —SH, —PO$_3$H$_2$, —PO$_2$H, =O, =S, =N—, —NH— and —NH$_2$ and capable of forming a dative or coordinate bond with a metal, this group preferably being a $C_3$ to $C_6$ cyclic, or $C_1$ to $C_6$ linear or branched, saturated or unsaturated hydrocarbon group substituted with one or more of the abovementioned functions.

Of course, when the compound is intended to be grafted in an MPHOIM in which the inorganic phase is designed to consist of two different metal oxides, it is possible for the compound to include two different functional groups for the grafting thereof, by covalent or iono-covalent bonding, in this MPHOIM.

Thus, for example, for an MPHOIM based on silicon oxide and on zirconium oxide, the compound may be such that at least one of $R^1$, $R^2$ and $R^3$ represents a group $—(Z)_z K$ in which K is a group $—Si(Cl)_m(OR^4)_n(R^5)_p$ as defined above, and/or that at least one of $R^1$, $R^2$ and $R^3$ represents a group $—(Z)_z K$ in which K is a metal-complexing group.

According to a first particularly preferred arrangement of the compound according to the invention, the latter corresponds to at least one of general formulae (I) and (II) in which:

$X^1$ and $Y^1$ both represent an oxygen atom, $Y^2$ represents an —OH group;

v is 0, u and w are 1;

U and W represent a phenyl group;

$R^1$ represents a hydrogen or halogen atom, a —CN or —NO$_2$ group, a $C_3$ to $C_6$ cyclic, or $C_1$ to $C_6$ linear or branched, saturated or unsaturated hydrocarbon group, this hydrocarbon group optionally containing one or more oxygen, nitrogen or sulphur atoms, or else an aryl or heteroaryl group having a 5- or 6-membered ring, $R^2$ represents a hydrogen atom, while $R^3$ represents a group $—(Z)_z K$ in which z is 1, Z represents a $C_1$ to $C_3$ linear, saturated or unsaturated divalent hydrocarbon group, and K is as defined above.

An example of such a compound, which is suitable for being grafted in a silicon-based MPHOIM, is 1-phenyl-3-[4-(2-triethoxysilylvinyl)phenyl]propane-1,3-dione.

According to another particularly preferred arrangement of the compound according to the invention, the latter corresponds to at least one of general formulae (I) and (II) in which:

$X^1$ and $Y^1$ both represent an oxygen atom, $Y^2$ represents an —OH group;

u and v are 0, w is 1;

W represents a phenyl group;

$R^1$ represents a hydrogen or halogen atom, a —CN or —NO$_2$ group, a $C_3$ to $C_6$ cyclic, or $C_1$ to $C_6$ linear or branched, saturated or unsaturated hydrocarbon group, this hydrocarbon group optionally containing one or more oxygen, nitrogen or sulphur atoms, or else an aryl or heteroaryl group having a 5- or 6-membered ring, $R^2$ represents a hydrogen atom, while $R^3$ represents a group $—(Z)_z K$ in which z is 1, Z represents a $C_1$ to $C_3$ linear, saturated or unsaturated divalent hydrocarbon group, and K is as defined above.

An example of such a compound, which is also suitable for being grafted in a silicon-based MPHOIM, is 1-[4-(2-triethoxysilylvinyl)phenyl]butane-1,3-dione.

The compounds according to the invention can be obtained by methods of synthesis known in the prior art, such as reactions consisting of acylation of ketones (C. H. Hauser, F. W. Swamer, J. T. Adams, *Org. React.*, 8, 1954, 59-196) or derivatization of β-diketones (T. M. Harris, C. M. Harris, *Org. React.*, 17, 1969, 155-211). β-Hydroxy ketones which can be obtained by aldol condensation (A. T. Nielsen, W. J. Houlihan, *Org. React.*, 16, 1968, 1-438) are intermediate products that are important for the synthesis of β-diketones. Numerous variants of aldol condensation have been described, involving in particular boron enolates (C. J. Cowden, I. Paterson, *Org. React.*, 51, 1997, 3-200), tin enolates (T. Mukaiyama, S. Kobayashi, *Org. React.*, 46, 1994, 1-103) or activation of the coupling of enoxysilanes with aldehydes by Lewis acids such as titanium tetrachloride (T. Mukaiyama, *Org. React.*, 28, 1982, 203-331).

The β-diketones can subsequently make it possible to obtain compounds containing nitrogenous complexing entities (S. G. McGeachin, *Can. J. Chem.*, 46, 1968, 1903-1912; N. Kuhn, S. Fuchs, M. Steimann, *Eur. J. Inorg. Chem.*, 2001, 359-361) or sulphur-containing complexing entities (S. Lanza, F. Nicolo, F. Tresoldi, *Eur. J. Inorg. Chem.*, 2002, 1049-1055).

A subject of the invention is also an MPHOIM which can be obtained by means of a sol-gel type process which comprises:

a) hydrolysis of at least one metal compound of general formula (III) below:

$$M(Cl)_q(OR^6)_r \qquad \text{(III)}$$

in which:
M is a metal as defined above;
q and r are integers ranging from 0 to the valency of M, with the proviso, however, that q+r is equal to this valency;
$R^6$ represents an organic group; in solution in a mixture of water, of an organic solvent and of an acid;
b) condensation of the product obtained in step a) in solution in a mixture comprising, in addition to water, said organic solvent and said acid, a surfactant;
c) reaction of the product obtained in step b) with at least one compound corresponding to at least one of general formulae (I) and (II) represented above, in which:
$X^1$ and $Y^1$ represent, independently of one another, an oxygen or sulphur atom or an =NH group;
$Y^2$ represents an —OH, —SH or —$NH_2$ group;
u, v and w are, independently of one another, 0 or 1, with the proviso, however, that at least one of u, v and w is other than 0;
U, V and W represent, independently of one another, an aryl or heteroaryl group having one or more rings, each having 5 or 6 ring members;
at least one of $R^1$, $R^2$ and $R^3$ represents a group —$(Z)_z$K in which z is 0 or 1, Z represents a $C_3$ to $C_6$ cyclic, or $C_1$ to $C_6$ linear or branched, saturated or unsaturated divalent hydrocarbon group, this hydrocarbon group optionally containing one or more oxygen, nitrogen or sulphur atoms; and in which:
when M is silicon or aluminium in the compound of general formula (III) used in step a), then K represents a group —$Si(Cl)_m(OR^4)_n(R^5)_p$ in which m and n are integers ranging from 0 to 3, p is an integer ranging from 0 to 2, with the proviso, however, that m+n is equal to 1, 2 or 3 and m+n+p is equal to 3; $R^4$ and $R^5$ represent, independently of one another, a $C_3$ to $C_6$ cyclic, or $C_1$ to $C_6$ linear or branched, saturated or unsaturated hydrocarbon group, this hydrocarbon group optionally containing one or more oxygen, nitrogen or sulphur atoms, or else an aryl or heteroaryl group having a 5- or 6-membered ring; whereas
when M is a metal other than silicon in the compound of general formula (III) used in step a), then K represents a metal-complexing group;
and in which that or those of $R^1$, $R^2$ and $R^3$ which does not or do not represent a group —$(Z)_z$K, if there is one, represent(s) a hydrogen or halogen atom, a —CN or —$NO_2$ group, a $C_3$ to $C_6$ cyclic, or $C_1$ to $C_6$ linear or branched, saturated or unsaturated hydrocarbon group, this hydrocarbon group optionally containing one or more oxygen, nitrogen or sulphur atoms, or else an aryl or heteroaryl group having a 5- or 6-membered ring;
d) thermal treatment of the product obtained in step c);
it being possible for steps a), b) and c) to be carried out simultaneously.

According to a preferred arrangement of the invention, the metal M of the compound of general formula (III) used in step a) is chosen from silicon, aluminium, zirconium, titanium, niobium, yttrium, vanadium and cerium, while the organic group $R^6$ of this compound is a $C_1$ to $C_6$, preferably $C_1$ to $C_3$, and better still $C_2$, alkyl group.

Preferably, the metal M of the compound of general formula (III) is silicon.

In this case, K of the group —$(Z)_z$K constituting at least one of $R^1$, $R^2$ and $R^3$ of the compound corresponding to at least one of general formulae (I) and (II) preferably represents a group chosen from the groups —$SiCl_3$, —$SiCl_2(OR^4)$, —$SiCl(OR^4)_2$ and —$Si(OR^4)_3$ where $R^4$ is a $C_1$ to $C_6$, preferably $C_1$ to $C_3$, alkyl group, and better still an ethyl group.

According to a preferred embodiment of this process, step a) is carried out using an alcohol as organic solvent, preferably ethanol, and hydrochloric acid as acid, and by heating the solution of compound of general formula (III), for example at a temperature of the order of 60 to 80° C. for approximately 1 hour.

Also according to this preferred embodiment, step b) is carried out at ambient temperature using cetyltrimethylammonium bromide as surfactant.

Still according to this preferred embodiment, step c) is, itself, carried out by reacting, at ambient temperature, the compound corresponding to at least one of general formulae (I) and (II) in solution in an organic solvent, advantageously tetrahydrofuran, with the product obtained in step b).

In step b), it is possible to add, to the solution comprising water, an organic solvent, an acid and a surfactant, a second organic solvent capable of promoting, in step c), the solubilization of the compound corresponding to at least one of formulae (I) and (II), in which case this second organic solvent is the same as that in which this compound finds itself when it is reacted in solution, in step c), with the product obtained in step b).

Again according to this preferred embodiment of the process, the thermal treatment in step d) consists in subjecting the product obtained in step c) to a temperature of 120 to 160° C. for a period of 24 to 72 hours so as to obtain evaporation of the various solvents present in this product and consolidation of its organic phase.

This thermal treatment is advantageously followed by washing, for example, with ethanol, with a view to eliminating from the material the surfactant and the other residues that it is liable to contain.

Particularly preferably, the process which has just been described comprises, in addition, between steps c) and d), a step in which the product obtained in step c) is made into the form of a thin film, for example by means of the dip coating technique, by spin coating or by spray coating on a support of the quartz, glass or silicon slide type, with a view to its use as a sensitive material and sensor.

Of course, the product obtained in step c) can just as easily be made into the form of a monolithic block if the use for which it is intended justifies this.

The material thus obtained is a porous material, which is both inorganic and organic, which has an organized porosity on the nanometre scale conferring on said films or monoliths a periodic structure of cubic, mixed cubic-2D-hexagonal, 2D-hexagonal or lamellar type, and the pores of which house the functional group of the compound corresponding to at least one of general formulae (I) and (II) which is capable of reacting with a halogenated gaseous compound and of forming with the latter a complex detectable by fluorescence spectrometry or absorption spectrometry.

The periodic structure of the material can advantageously be controlled, in particular by adjusting the respective proportions of the compound of general formula (III), of the surfactant and of the compound corresponding to at least one of general formulae (I) and (II), just as the diameter of the pores of the organized porosity can be controlled through the choice of the surfactant.

By means of the process which has just been described, it is possible to produce an MPHOIM made up of several different metal oxides, in which case step a) of the process comprises the hydrolysis of several compounds of general formula (III):

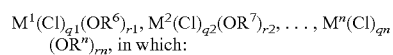
in which:

$M^1, M^2, \ldots, M^n$ represent metals different from one another;

q1 and r1 are integers ranging from 0 to the valency of $M^1$ with q1+r1 which is equal to this valency;

q2 and r2 are integers ranging from 0 to the valency of $M^2$ with q2+r2 which is equal to this valency;

qn and rn are integers ranging from 0 to the valency of $M^n$ with qn+rn which is equal to this valency; and $R^6, R^7, \ldots, R^n$ represent, independently of one another, an organic group.

According to the nature of $M^1, M^2, \ldots, M^n$, step c) can be carried out using a single compound corresponding to at least one of general formulae (I) and (II), if the latter has the functional group(s) suitable for grafting thereof in this MPHOIM, or a mixture of several compounds corresponding to at least one of general formulae (I) and (II).

A subject of the invention is also a process for manufacturing an MPHOIM which can be used as sensitive material in a sensor for the detection or quantitative determination of halogenated gaseous compounds, this process being as defined above.

A subject of the invention is also a sensor which can be used for the detection or quantitative determination of halogenated gaseous compounds, comprising an MPHOIM as defined above, as sensitive material.

Preferably, this sensor is intended for the detection or quantitative determination of halogenated boron complexes, in particular $BF_3$ and $BCl_3$.

A subject of the invention is also the use of a compound corresponding to at least one of general formulae (I) and (II) represented above, in which:

$X^1$ and $Y^1$ represent, independently of one another, an oxygen or sulphur atom or an =NH group;

$Y^2$ represents an —OH, —SH or —$NH_2$ group;

u, v and w are, independently of one another, 0 or 1, with the proviso, however, that at least one of u, v and w is other than 0;

U, V and W represent, independently of one another, an aryl or heteroaryl group having one or more rings, each having 5 or 6 ring members;

at least one of $R^1$, $R^2$ and $R^3$ represents a group —$(Z)_z K$ in which:

z is 0 or 1, Z represents a $C_3$ to $C_6$ cyclic, or $C_1$ to $C_6$ linear or branched, saturated or unsaturated divalent hydrocarbon group, this hydrocarbon group optionally containing one or more oxygen, nitrogen or sulphur atoms; and K represents:

either a group —$Si(Cl)_m(OR^4)_n(R^5)_p$ in which:

m and n are integers ranging from 0 to 3, p is an integer ranging from 0 to 2, with the proviso, however, that m+n is equal to 1, 2 or 3 and m+n+p is equal to 3;

$R^4$ and $R^5$ represent, independently of one another, a $C_3$ to $C_6$ cyclic, or $C_1$ to $C_6$ linear or branched, saturated or unsaturated hydrocarbon group, this hydrocarbon group optionally containing one or more oxygen, nitrogen or sulphur atoms, or else an aryl or heteroaryl group having a 5- or 6-membered ring;

or a metal-complexing group;

and in which that or those of $R^1$, $R^2$ and $R^3$ which does not or do not represent a group —$(Z)_z K$, if there is one, represent(s) a hydrogen or halogen atom, a —CN or —$NO_2$ group, a $C_3$ to $C_6$ cyclic, or $C_1$ to $C_6$ linear or branched, saturated or unsaturated hydrocarbon group, this hydrocarbon group optionally containing one or more oxygen, nitrogen or sulphur atoms, or else an aryl or heteroaryl group having a 5- or 6-membered ring; as probe molecule for the detection or quantitative determination of halogenated gaseous compounds, especially halogenated boron complexes, in particular $BF_3$ and $BCl_3$.

The invention will be understood more clearly upon reading the further description which follows, which refers to examples of synthesis of compounds and of MPHOIM in accordance with the invention and also to examples of demonstration of the usefulness of such MPHOIMs as sensitive materials of a sensor for the detection of halogenated gaseous compounds, and which refers to the attached drawings.

It goes without saying that this additional description is given by way of illustration of the invention and should in no way be considered to be a limitation of the subject of the invention.

DETAILED DISCLOSURE OF SPECIFIC EMBODIMENTS

Example 1

Synthesis of 1-phenyl-3-[4-(2-triethoxysilylvinyl) phenyl]propane-1,3-dione

Figure 1:
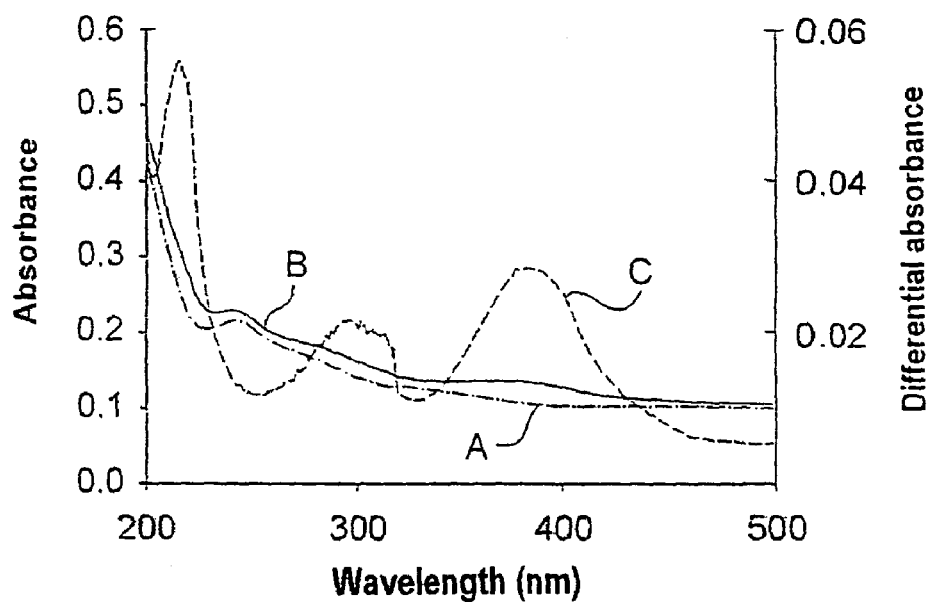
FIG. 1 is a graph illustrating the evolution of the absorbance spectrum of a thin film consisting of an MPHOIM in accordance with the invention, which is cubic in structure, as obtained in the absence of $BF_3$ (curve A) and after complete reaction of the compound present as probe molecule in this film with $BF_3$ (curve B), and also the differential absorbance of this film (curve C).

The title compound, or compound 1, of specific formula (Ia) below:

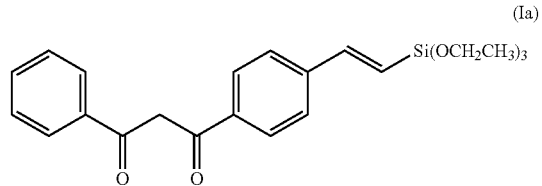

(Ia)

is obtained by reacting 1-phenyl-3-(4-bromophenyl)-propane-1,3-dione, or compound 5, with triethoxyvinylsilane.

1.1. Synthesis of Compound 5

Compound 5 is prepared by reacting 4-bromo-acetophenone (2.99 g, 15 mmol) with methyl benzoate (4.08 g, 30 mmol) according to the procedure described by V. V. Popic, S. M. Korneev, V. A. Nicolaev, I. K. Korobitsyna in *Synthesis*, 1991, 195-197.

2.59 g (8.6 mmol) of compound 5 are thus obtained.

1.2. Synthesis of Compound 1

20 ml of freshly distilled dimethyl-formamide (DMF), 2.8 ml (20.0 mmol) of triethylamine and 1.7 ml (8.0 mmol) of triethoxyvinylsilane are added to a double-necked flask, under argon, containing 2.0 g (6.6 mmol) of compound 5, 5.9 mg (0.026 mmol) of palladium acetate and 48.0 mg (0.16 mmol) of tri-o-toluoylphosphine $P(o-C_6H_4-CH_3)_3$. The resulting solution is heated to 100° C. and left at this temperature for 18 hours, after which the reaction mixture is left to return to ambient temperature and is filtered. The solvents are evaporated off under vacuum, and the heterogeneous residue obtained is dissolved in diethyl ether. After filtration and evaporation of the solvent, 2.5 g (5.7 mmol) of compound 1, which is in the form of a highly viscous orange oil, are obtained with a yield of 87%.

$^1$H NMR (CDCl$_3$, δ ppm): 1.26 (t, 9H, J=7.0 Hz), 3.91 (q, 6H, J=7.0 Hz), 6.32 (d, 1H, J=19.3 Hz), 6.86 (s, 1H), 7.08 (d, 1H, J=19.4 Hz), 7.47-7.59 (m, 5H), 7.95-7.99 (m, 5H), 11.69 (bs, 1H)

$^{13}$C NMR-(CDCl$_3$, δ ppm): 18.3, 58.7, 93.2, 121.1, 127.0, 127.2, 127.5, 128.7, 132.5, 135.4, 135.5, 141.4, 147.7, 184.8, 186.0

$^{29}$Si NMR (CDCl$_3$, δ ppm): −57.2 (s)

FT-IR (KBr, ν$_{max}$/cm$^{-1}$): 2975, 2888, 1603, 1077, 960, 821, 769

Mass (Fab) (M+H)$^+$: calculated: 413.1821; found: 413.1784

Elemental analysis: calculated: C=66.96%, H=6.84%; found: C=67.24%, H=6.86%

Example 2

Synthesis of 1-[4-(2-triethoxysilylvinyl)-phenyl] butane-1,3-dione

The title compound, or compound 2, of specific formula (Ib) below:

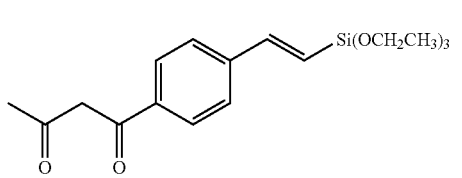

is obtained by reacting 1-[4-bromophenyl]butane-1,3-dione, or compound 6, with triethoxyvinylsilane.

2.1. Synthesis of Compound 6

Compound 6 is prepared by reacting 4-bromo-acetophenone (4.98 g, 25 mmol) with ethyl acetate (4.41 g, 50 mmol) according to the procedure described by V. V. Popic, S. M. Korneev, V. A. Nicolaev, I. K. Korobitsyna in *Synthesis*, 1991, 195-197.

4.88 g (20.3 mmol) of compound 6 are thus obtained.

2.2. Synthesis of Compound 2

40 ml of freshly distilled DMF, 8.7 ml (63 mmol) of triethylamine and 5.45 ml (25.7 mmol) of triethoxyvinylsilane are added to a double-necked flask, under argon, containing 5.0 g (20.9 mmol) of compound 6, 14 mg (0.063 mmol) of palladium acetate and 75 mg (0.25 mmol) of $P(o-C_6H_4-CH_3)_3$. The resulting solution is heated to 100° C. and left at this temperature for 18 hours, after which the reaction mixture is left to return to ambient temperature and is filtered. The solvents are evaporated off under vacuum, and the heterogeneous residue obtained is dissolved in diethyl ether. After filtration and evaporation of the solvent, 6.84 g (19.5 mmol) of compound 2, which is in the form of a highly viscous orange oil, are obtained with a yield of 93%.

$^1$H NMR (CDCl$_3$, δ ppm): 1.25 (t, 9H, J=7.0 Hz), 2.17 (s, 3H), 3.87 (q, 6H, J=7.0 Hz), 6.15 (s, 1H), 6.27 (d, 1H, J=19.3 Hz), 7.21 (d, 1H, 19.4 Hz), 7.48-7.53 (m, 2H), 7.81-7.86 (m, 2H), 11.69 (bs, 1H);

$^{13}$C NMR (CDCl$_3$, δ ppm): 18.2, 25.9, 58.7, 96.7, 121.0, 126.9, 127.3, 134.7, 141.2, 147.7, 182.3, 194.0;

FT-IR (KBr, ν$_{max}$/cm$^{-1}$): 2975, 2926, 2887, 1606, 1295, 1167, 1080, 962, 829, 783;

Mass (Fab) (M+H)$^+$: calculated: 351.1627; found: 351.1617.

Example 3

Synthesis of MPHOIM in Accordance with the Invention

MPHOIMs in accordance with the invention are produced by preparing a synthesis sol from a solution of tetraethoxysilane (TEOS) hydrolysed beforehand, and then reacting the sol thus obtained with concentrated solutions of compound 1 or 2.

To do this, TEOS, absolute ethanol, hydrochloric acid 2M/720 and deionized water are mixed in a molar ratio of 1 TEOS/3 EtOH/5·10$^{-5}$ HCl/1H$_2$O, and the mixture is heated at 70° C. for 1 hour. The order of addition of the various compounds is not important and has no effect on the quality of the resulting solution.

The synthesis sol is prepared by addition of cetyltrimethylammonium bromide (CTAB), absolute ethanol, tetrahydrofuran (THF), deionized water and 2M/36 or 2M hydrochloric acid (as chosen, as explained below) to the solution of prehydrolysed TEOS prehydrolyse. Here also, the addition of the various compounds is a free choice and has no effect on the quality of the resulting solutions.

In the case of the use of 2M/36 hydrochloric acid, the molar ratio of the synthesis sol is 0.14 CTAB/1 TEOS/6 EtOH/9 THF/5H$_2$O/0.004 HCl, and in the case of the use of 2M hydrochloric acid, the molar ratio of the synthesis sol is 0.14 CTAB/1 TEOS/6 EtOH/9 THF/5 H$_2$O/0.15 HCl.

The sol having the lowest HCl content is used 5 days after it has been prepared and for up to about ten days if it is stored at ambient temperature (and longer if it is kept at 4° C.), while the sol having the highest HCl content is used the day after it was prepared and for up to 3-4 days (and longer if it is kept at 4° C.).

In the two cases, concentrated (typically 1 M) solutions of compound 1 or 2 in THF are added to the synthesis sol so as to obtain solutions with a molar ratio of 0.14 CTAB/1 TEOS/6 EtOH/9 THF/5H$_2$O/0.004-0.15 HCl/5·10$^{-3}$-0.15 compound 1 or 2, which are stirred at ambient temperature for 15 minutes.

In order to produce the MPHOIMs in the form of thin films, the dip coating technique is used on quartz, glass or silicon supports. The supports are soaked in the sol, and then removed at a rate of 2.5 mm/s.

The relative humidity is controlled during the drying of the films. Thus, it is 40% for the first 30 seconds, and then 70% for 5 minutes.

Once prepared, the films are kept at 140° C. for 48 hours, and the CTAB is then eliminated by washing with absolute ethanol.

As shown in Table 1 below, the structure of the films thus obtained is cubic, mixed cubic-2D-hexagonal, 2D-hexagonal and lamellar according to the molar percentage of compound 1 or 2 relative to the silicon (i.e. the ratio of the number of moles of compound 1 or 2 present in the films to the total number of moles of silicon present in the films, multiplied by 100).

TABLE 1

| Structure | Cubic | Mixed cubic-2D-hexagonal | 2D-hexagonal | Lamellar |
|---|---|---|---|---|
| molar % compound/Si | 0~0.7 | ~1.0 | 1.4~2.5 | 5.3~15.0 |

Example 4

Demonstration of the Usefulness of MPHOIMs in Accordance with the Invention as Sensitive Materials of a Sensor for the Detection of Halogenated Gaseous Compounds To demonstrate the usefulness of the MPHOIMs in accordance with the invention as sensitive materials of a sensor for the detection of halogenated gaseous compounds, thin films of MPHOIMs as obtained in Example 3 above, and comprising compound 1 as probe molecule, optionally in equilibrium with its enol form, are treated with $BF_3$ by means of a device identical to that illustrated in FIG. 1 of FR-A-2 840 547.

Briefly, this device, which was designed to allow the incorporation of a gaseous compound into the pores of a porous material, is composed of a quartz cuvette with four optical faces and a stopper able to hermetically close this cuvette.

The cuvette is equipped with a ground socket at its upper end.

The stopper comprises, itself, a ground cone at its lower end, which is able to fit into the ground socket in the cuvette so as to provide hermetic closure of the latter, and a vacuum tap at its upper end. This stopper is, in addition, equipped on the side with an elbow tube which can be connected to a vacuum system.

A Teflon® cylinder which is attached to the bottom of the cuvette makes it possible to maintain vertically a thin film covering one or the two faces of a support by means of a groove that it comprises.

After having placed one of the thin films to be tested in the cuvette, 500 μl of a commercial solution of boron trifluoride etherate ($BF_3$-$(Et)_2O$) are deposited at the bottom of this cuvette. Before placing the device under a partial vacuum, the cuvette is kept at low temperature in liquid nitrogen or a dry ice and alcohol bath so as to prevent, during the establishment of the vacuum, the solution of $BF_3$-$(Et)_2O$ being evaporated. After pumping and production of the desired vacuum ($10^{-5}$ torr) in the cuvette, the latter is isolated from the rest of the device and immersed in a bath of oil maintained at a temperature of 50° C., allowing the $BF_3$-$(Et)_2O$ complex to dissociate and to release the $BF_3$.

The reaction between the latter and compound 1 present in each thin film is monitored optically by collecting the absorption and fluorescence spectra for this film at regular intervals (i.e. every hour).

Figure 2:
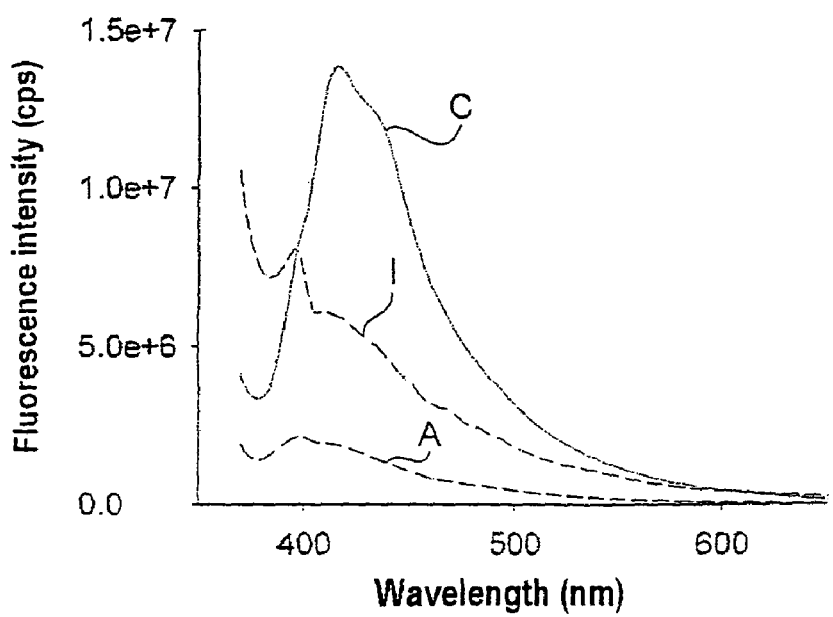
FIG. 2 is a graph illustrating the evolution of the fluorescence spectrum of a thin film consisting of an MPHOIM in accordance with the invention, which is cubic in structure, as obtained in the absence of $BF_3$ (curve A), after partial reaction and after complete reaction of the compound present as probe molecule in this film with $BF_3$ (curves I and C), for an excitation wavelength of 356 nm.
Figure 3:
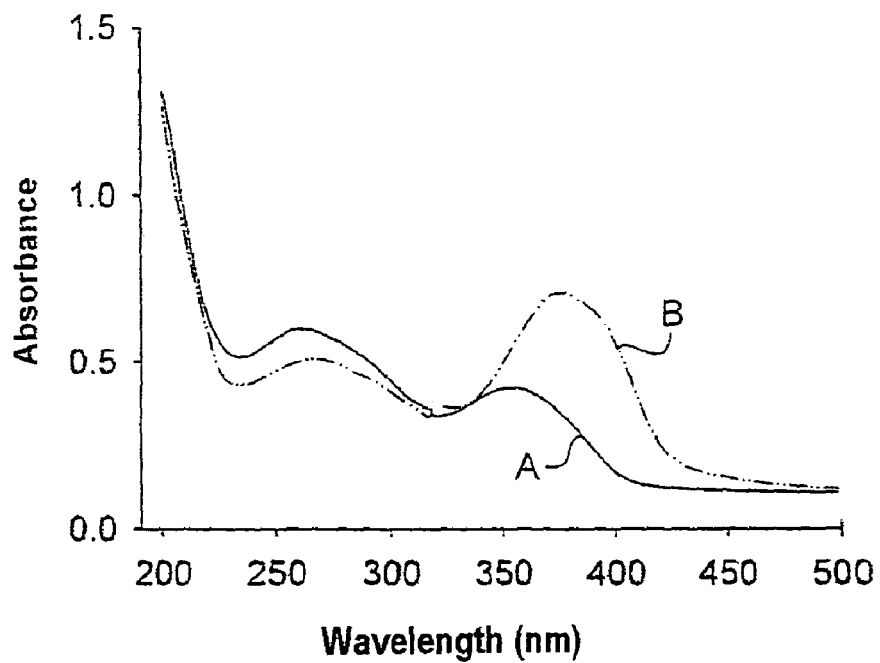
FIG. 3 is a graph illustrating the evolution of the absorbance spectrum of a thin film consisting of an MPHOIM in accordance with the invention, which is lamellar in structure, as obtained in the absence of $BF_3$ (curve A) and after complete reaction of the compound present as probe molecule in this film with $BF_3$ (curve B).
Figure 4:
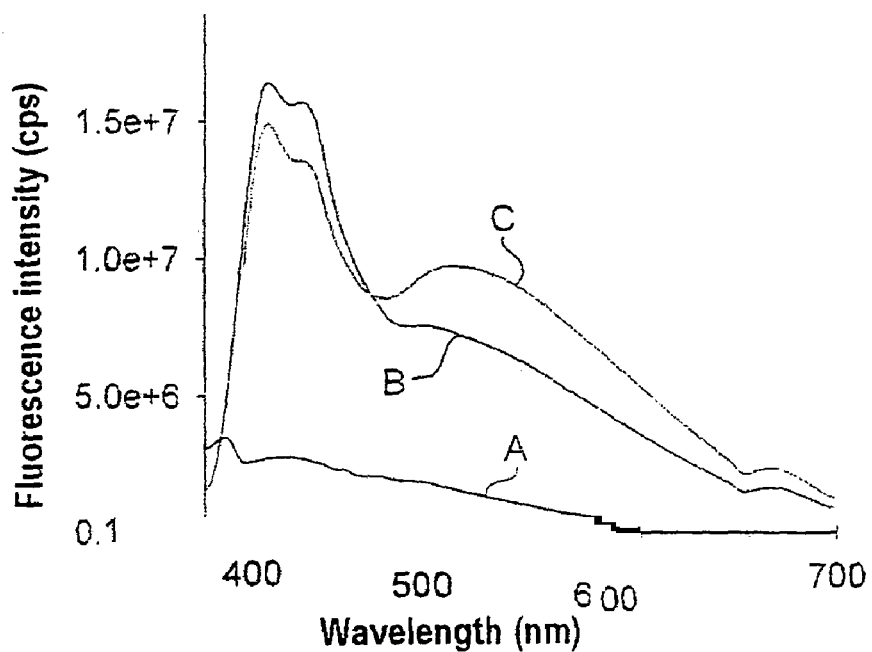
FIG. 4 is a graph illustrating the evolution of the fluorescence spectrum of a thin film consisting of an MPHOIM in accordance with the invention, which is lamellar in structure, as obtained in the absence of $BF_3$ for an excitation wavelength of 356 nm (curve A) and after complete reaction of the compound present as probe molecule in this film with $BF_3$, for an excitation wavelength of, respectively, 356 nm (curve B) and 375 nm (curve C).

The results are illustrated in FIGS. 1 to 4, which represent:

FIG. 1: the evolution of the absorbance spectrum of a thin film, which is cubic in structure and comprises compound 1 as probe molecule, as obtained in the absence of $BF_3$ (curve A) and after complete reaction (reaction time=3 hours) of the compound 1 present in this film with $BF_3$ (curve B), and also the differential absorbance of this film (curve C=curve B−curve A);

FIG. 2: the evolution of the fluorescence spectrum obtained for a thin film, which has a cubic structure and comprises compound 1 as probe molecule, as obtained in the absence of $BF_3$ (curve A), after partial reaction (reaction time=1 hour) and after complete reaction (reaction time=3 hours) of the compound 1 present in this film with $BF_3$ (curves I and C), for an excitation wavelength of 356 nm;

FIG. 3: the evolution of the absorbance spectrum of a thin film, which has a lamellar structure and comprises compound 1 as probe molecule (partially in enol form), as obtained in the absence of $BF_3$ (curve A) and after complete reaction (reaction time=8 hours) of the compound 1 present in this film with $BF_3$ (curve B);

FIG. 4: evolution of the fluorescence spectrum of a thin film, which has a lamellar structure and comprises compound 1 as probe molecule, in the absence of $BF_3$ for an excitation wavelength of 356 nm (curve A), and after complete reaction (reaction time=8 hours) of the compound 1 present in this film with $BF_3$, for an excitation wavelength of, respectively, 356 nm (curve B) and 375 nm (curve C).

The invention claimed is:

1. Compound corresponding to at least one of the general formulae (I) and (II) below:

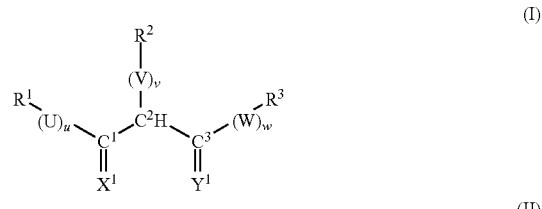

(I)

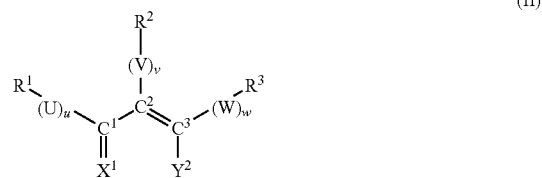

(II)

in which:

$X^1$ and $Y^1$ represent, independently of one another, an oxygen or sulphur atom or an =NH group;

$Y^2$ represents an —OH, —SH or —$NH_2$ group;

u, v and w are, independently of one another, 0 or 1, with the proviso, however, that at least one of u, v and w is other than 0;

U, V and W represent, independently of one another, an aryl or heteroaryl group having one or more rings, each having 5 or 6 ring members;

at least one of $R^1$, $R^2$ and $R^3$ represents a group —$(Z)_zK$ in which:

z is 0 or 1, Z represents a $C_3$ to $C_6$ cyclic, or $C_1$ to $C_6$ linear or branched, saturated or unsaturated divalent hydrocarbon group, this hydrocarbon group optionally containing one or more oxygen, nitrogen or sulphur atoms; and K represents:

either a group —Si(Cl)$_m$(OR$^4$)$_n$(R$^5$)$_p$ in which:

m and n are integers ranging from 0 to 3, p is an integer ranging from 0 to 2, with the proviso, however, that m+n is equal to 1, 2 or 3 and m+n+p is equal to 3;

R$^4$ and R$^5$ represent, independently of one another, a $C_3$ to $C_6$ cyclic, or $C_1$ to $C_6$ linear or branched, saturated or unsaturated hydrocarbon group, this hydrocarbon group optionally containing one or more oxygen, nitrogen or sulphur atoms, or else an aryl or heteroaryl group having a 5- or 6-membered ring;

or a metal-complexing group;

and in which that or those of R$^1$, R$^2$ and R$^3$ which does not or do not represent a group —(Z)$_z$K, if there is one, represent(s) a hydrogen or halogen atom, a —CN or —NO$_2$ group, a $C_3$ to $C_6$ cyclic, or $C_1$ to $C_6$ linear or branched, saturated or unsaturated hydrocarbon group, this hydrocarbon group optionally containing one or more oxygen, nitrogen or sulphur atoms, or else an aryl or heteroaryl group having a 5- or 6-membered ring;

with the exclusion of compounds in which one of R$^1$ and R$^3$ represents a group —O(CH$_2$)$_3$—Si(OR$^4$)$_n$(R$^5$)$_p$ when U and W both represent a phenyl group, v is 0, R$^2$ represents a hydrogen atom, X$^1$ and Y$^1$ both represent an oxygen atom or X$^1$ represents an oxygen atom and Y$^2$ represents an —OH group.

2. Compound according to claim 1, which corresponds to at least one of general formulae (I) and (II) in which X$^1$ and Y$^1$ represent an oxygen atom, Y$^2$ represents an —OH group, and u, v, w, U, V, W, R$^1$, R$^2$ and R$^3$ are as defined above.

3. Compound according to claim 1, which corresponds to at least one of general formulae (I) and (II) in which v is 0, u and w are 1, and U, W, X$^1$, Y$^1$, Y$^2$, R$^1$, R$^2$ and R$^3$ are as defined above.

4. Compound according to claim 1, which corresponds to at least one of general formulae (I) and (II) in which u and v are 0, w is 1, and W, X$^1$, Y$^1$, Y$^2$, R$^1$, R$^2$ and R$^3$ are as defined above.

5. Compound according to claim 1, in which K of the group —(Z)$_z$K constituting at least one of R$^1$, R$^2$ and R$^3$ represents a group chosen from the groups —SiCl$_3$, —SiCl$_2$(OR$^4$), —SiCl(OR$^4$)$_2$ and —Si(OR$^4$)$_3$ where R$^4$ is a $C_1$ to $C_6$ alkyl group.

6. Compound according to claim 1, in which K of the group —(Z)$_1$K constituting at least one of R$^1$, R$^2$ and R$^3$ represents a $C_3$ to $C_6$ cyclic, or $C_1$ to $C_6$ linear or branched, saturated or unsaturated hydrocarbon group substituted with several functions chosen from —OH, —COOH, —NH$_2$, =NOH, —SH, —PO$_3$H$_2$, —PO$_2$H, =O, =S, =N—, —NH— and —NH$_2$.

7. Compound according to claim 1, which corresponds to at least one of general formulae (I) and (II) in which:

X$^1$ and Y$^1$ both represent an oxygen atom, Y$^2$ represents an —OH group;

v is 0 and u; and w are 1;

U and W represent a phenyl group;

R$^1$ represents a hydrogen or halogen atom, a —CN or —NO$_2$ group, a $C_3$ to $C_6$ cyclic, or $C_1$ to $C_6$ linear or branched, saturated or unsaturated hydrocarbon group, this hydrocarbon group optionally containing one or more oxygen, nitrogen or sulphur atoms, or else an aryl or heteroaryl group having a 5- or 6-membered ring, R$^2$ represents a hydrogen atom, while R$^3$ represents a group —(Z)$_z$K in which z is 1, Z represents a $C_1$ to $C_3$ linear, saturated or unsaturated divalent hydrocarbon group, and K is as defined above.

8. Compound according to claim 7, which is 1-phenyl-3-[4-(2-triethoxysilylvinyl)phenyl]propane-1,3-dione.

9. Compound according to claim 1, which corresponds to at least one of general formulae (I) and (II) in which:

X$^1$ and Y$^1$ both represent an oxygen atom, Y$^2$ represents an —OH group;

u and v are 0, w is 1;

W represents a phenyl group;

R$^1$ represents a hydrogen or halogen atom, a —CN or —NO$_2$ group, a $C_3$ to $C_6$ cyclic, or $C_1$ to $C_6$ linear or branched, saturated or unsaturated hydrocarbon group, this hydrocarbon group optionally containing one or more oxygen, nitrogen or sulphur atoms, or else an aryl or heteroaryl group having a 5- or 6-membered ring, R$^2$ represents a hydrogen atom, while R$^3$ represents a group —(Z)$_z$K in which z is 1, Z represents a $C_1$ to $C_3$ linear, saturated or unsaturated divalent hydrocarbon group, and K is as defined above.

10. Compound according to claim 9, which is 1-[4-(2-triethoxysilylvinyl)phenyl]butane-1,3-dione.

11. Mesostructured porous hybrid organic-inorganic material prepared by a sol-gel process which comprises:

a) hydrolysis of at least one metal compound of general formula (III) below:

in which:

M is a metal;

q and r are integers ranging from 0 to the valency of M, with the proviso, however, that q+r is equal to this valency; and R$^6$ represents an organic group;

in solution in a mixture of water, of an organic solvent and of an acid;

b) condensation of the product obtained in step a) in solution in a mixture containing, in addition to water, said organic solvent and said acid, a surfactant;

c) reaction of the product obtained in step b) with at least one compound corresponding to at least one of general formulae (I) and (II) below:

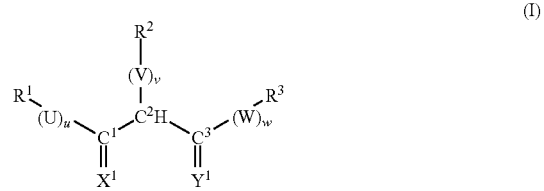

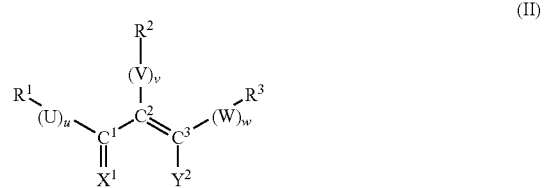

in which:

X$^1$ and Y$^1$ represent, independently of one another, an oxygen or sulphur atom or an =NH group;

Y$^2$ represents an —OH, —SH or —NH$_2$ group;

u, v and w are, independently of one another, 0 or 1, with the proviso, however, that at least one of u, v and w is other than 0;

U, V and W represent, independently of one another, an aryl or heteroaryl group having one or more rings, each having 5 or 6 ring members;

at least one of $R^1$, $R^2$ and $R^3$ represents a group —$(Z)_z K$ in which z is 0 or 1, Z represents a $C_3$ to $C_6$ cyclic, or $C_1$ to $C_6$ linear or branched, saturated or unsaturated divalent hydrocarbon group, this hydrocarbon group optionally containing one or more oxygen, nitrogen or sulphur atoms; and in which:

when M is silicon or aluminium in the compound of general formula (III) used in step a), then K represents a group —$Si(Cl)_m(OR^4)_n(R^5)_p$ in which m and n are integers ranging from 0 to 3, p is an integer ranging from 0 to 2, with the proviso, however, that m+n is equal to 1, 2 or 3 and m+n+p is equal to 3; $R^4$ and $R^5$ represent, independently of one another, a $C_3$ to $C_6$ cyclic, or $C_1$ to $C_6$ linear or branched, saturated or unsaturated hydrocarbon group, this hydrocarbon group optionally containing one or more oxygen, nitrogen or sulphur atoms, or else an aryl or heteroaryl group having a 5- or 6-membered ring; whereas when M is a metal other than silicon in the compound of general formula (III) used in step a), then K represents a metal-complexing group;

and in which that or those of $R^1$, $R^2$ and $R^3$ which does not or do not represent a group —$(Z)_z K$, if there is one, represent(s) a hydrogen or halogen atom, a —CN or —$NO_2$ group, a $C_3$ to $C_6$ cyclic, or $C_1$ to $C_6$ linear or branched, saturated or unsaturated hydrocarbon group, this hydrocarbon group optionally containing one or more oxygen, nitrogen or sulphur atoms, or else an aryl or heteroaryl group having a 5- or 6-membered ring;

d) thermal treatment of the product obtained in step c);

steps a), b) and c) optionally being carried out simultaneously.

12. Mesostructured porous hybrid organic-inorganic material according to claim 11, prepared by a process in which the metal M of the compound of general formula (III) is chosen from silicon, aluminium, zirconium, titanium, niobium, yttrium, vanadium and cerium.

13. Mesostructured porous hybrid organic-inorganic material according to claim 11 prepared by a process in which the organic group $R^6$ of the compound of general formula (III) is a $C_1$ to $C_6$ alkyl group.

14. Mesostructured porous hybrid organic-inorganic material according to claim 11, prepared by a process in which the metal M of the compound of general formula (III) is silicon.

15. Mesostructured porous hybrid organic-inorganic material according to claim 14 prepared by a process in which K of the group —$(Z)_z K$ constituting at least one of $R^1$, $R^2$ and $R^3$ of the compound corresponding to at least one of general formulae (I) and (II) represents a group chosen from the groups —$SiCl_3$, —$SiCl_2(OR^4)$, —$SiCl(OR)_2$ and —$Si(OR^4)_3$ where $R^4$ is a $C_1$ to $C_6$ alkyl group.

16. Mesostructured porous hybrid organic-inorganic material according to claim 11, prepared by a process in which step a) is carried out using an alcohol as organic solvent, preferably ethanol, and hydrochloric acid as acid, and by heating the solution of compound of general formula (III).

17. Mesostructured porous hybrid organic-inorganic material according to claim 11, prepared by a process in which step b) is carried out at ambient temperature using cetyltrimethylammonium bromide as surfactant.

18. Mesostructured porous hybrid organic-inorganic material according to claim 11, prepared by a process in which step c) is carried out by reacting, at ambient temperature, the compound corresponding to at least one of general formulae (I) and (II) in solution in an organic solvent, with the product obtained in step b).

19. Mesostructured porous hybrid organic-inorganic material according to claim 1, prepared by a process in which, in step d), the thermal treatment consists in subjecting the product resulting from step c) to a temperature of 120 to 160° C. for a period of 24 to 72 hours.

20. Mesostructured porous hybrid organic-inorganic material according to claim 11, prepared by a process which comprises, in addition, between steps c) and d), a step in which the product obtained in step c) is made into the form of a thin film.

21. Mesostructured porous hybrid organic-inorganic material according to claim 11, prepared by a process in which step a) comprises the hydrolysis of several compounds of general formula (III): $M^1(Cl)_{q1}(OR^6)_{r1}$, $M^2(O)_{q2}(OR^7)_{r2}$, ..., $M^n(Cl)_{qn}(OR'')_{rn}$, in which:

$M^1$, $M^2$, ..., $M^n$ represent metals different from one another;

q1 and r1 are integers ranging from 0 to the valency of $M^1$ with q1+r1 which is equal to this valency;

q2 and r2 are integers ranging from 0 to the valency of $M^2$ with q2+r2 which is equal to this valency;

qn and rn are integers ranging from 0 to the valency of $M^n$ with qn+rn which is equal to this valency; and $R^6, R^7, \ldots, R''$ represent, independently of one another, an organic group.

22. Process for manufacturing a mesostructured porous hybrid organic-inorganic material used as sensitive material in a sensor for the detection or quantitative determination of halogenated gaseous compounds, which process comprises:

a) hydrolysis of at least one metal compound of general formula (III) in a mixture of water, of an organic solvent and of an acid:

$$M(Cl)_q(OR^6)_r \quad (III)$$

in which:

M is a metal;

q and r are integers ranging from 0 to the valency of M, with the proviso that q+r is equal to this valency; and $R^6$ represents an organic group;

b) condensing the product obtained in a) in a mixture comprising, in addition to water, said organic solvent and said acid, a surfactant;

c) reacting the product obtained in b) with at least one compound corresponding to at general formulae (I) and (II):

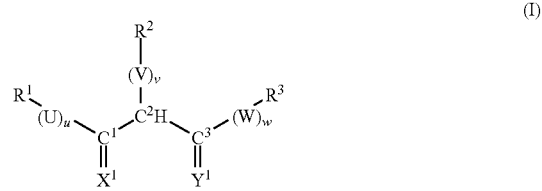

(I)

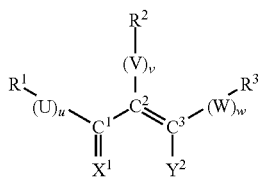
(II)

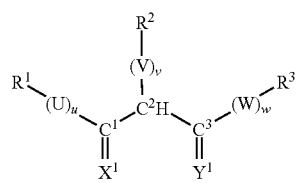
(I)

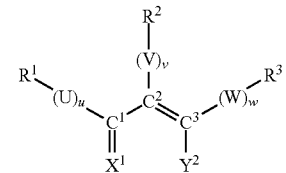
(II)

wherein $X^1$ and $Y^1$ represent, independently of one another, an oxygen, sulphur atom or an =NH group;

$Y^2$ represents an —OH, —SH or —NH$_2$ group;

u, v and w are, independently of one another, 0 or 1, with the proviso that at least one of u, v and w is other than 0;

U, V and W represent, independently of one another, an aryl or heteroaryl group having one or more rings, each having 5 or 6 ring members;

at least one of $R^1$, $R^2$ and $R^3$ represents a group —$(Z)_z$K in which z is 0 or 1, Z represents a $C_3$ to $C_6$ cyclic, or $C_1$ to $C_6$ linear or branched, saturated or unsaturated divalent hydrocarbon group, this hydrocarbon group optionally containing one or more oxygen, nitrogen or sulphur atoms; and in which:

when M is silicon or aluminium in the compound of general formula (III) then K represents a group —Si(Cl)$_m$(OR$^4$)$_n$(R$^5$)$_p$ in which m and n are integers ranging from 0 to 3, p is an integer ranging from 0 to 2, with the proviso that m+n is equal to 1, 2 or 3 and m+n+p is equal to 3; $R^4$ and $R^5$ represent, independently of one another a $C_3$ to $C_6$ cyclic, or $C_1$ to $C_6$ linear or branched, saturated or unsaturated hydrocarbon group, this hydrocarbon group optionally containing one or more oxygen, nitrogen or sulphur atoms, or else an aryl or heteroaryl group having a 5- or 6-membered ring; whereas when M is a metal other than silicon in the compound of general formula (III) used in step a), then K represents a metal-complexing group;

and in which that or those of $R^1$, $R^2$ and $R^3$ which does not or do not represent a group —$(Z)_z$K, if there is one, represent(s) a hydrogen or halogen atom, a —CN or —NO$_2$ group, a $C_3$ to $C_6$ cyclic, or $C_1$ to $C_6$ linear or branched, saturated or unsaturated hydrocarbon group, this hydrocarbon group optionally containing one or more oxygen, nitrogen or sulphur atoms, or else an aryl or heteroaryl group having a 5- or 6-membered ring; and d) thermally treating the product obtained in c);

wherein a), b) and c) are optionally carried out simultaneously.

23. A method for detecting the presence of a halogenated compound in a medium, which method comprises:

contacting the medium with a material having an optical property which is modified upon contact with a halogenated gaseous compound and comprising a compound corresponding to at least one of general formulae (I) and (II) below as a probe molecule:

in which:

$X^1$ and $Y^1$ represent, independently of one another, an oxygen or sulphur atom or an =NH group;

$Y^2$ represents an —OH, —SH or —NH$_2$ group;

u, v and w are, independently of one another, 0 or 1, with the proviso, however, that at least one of u, v and w is other than 0;

U, V and W represent, independently of one another, an aryl or heteroaryl group having one or more rings, each having 5 or 6 ring members;

at least one of $R^1$, $R^2$ and $R^3$ represents a group —$(Z)_z$K in which:

z is 0 or 1, Z represents a $C_3$ to $C_6$ cyclic, or $C_1$ to $C_6$ linear or branched, saturated or unsaturated divalent hydrocarbon group, this hydrocarbon group optionally containing one or more oxygen, nitrogen or sulphur atoms; and K represents:

either a group —Si(Cl)$_m$(OR$^4$)$_n$(R$^5$)$_p$ in which:

m and n are integers ranging from 0 to 3, p is an integer ranging from 0 to 2, with the proviso, however, that m+n is equal to 1, 2 or 3 and m+n+p is equal to 3;

$R^4$ and $R^5$ represent, independently of one another, a $C_3$ to $C_6$ cyclic, or $C_1$ to $C_6$ linear or branched, saturated or unsaturated hydrocarbon group, this hydrocarbon group optionally containing one or more oxygen, nitrogen or sulphur atoms, or else an aryl or heteroaryl group having a 5- or 6-membered ring;

or a metal-complexing group;

and in which that or those of $R^1$, $R^2$ and $R^3$ which does not or do not represent a group —$(Z)_z$K, if there is one, represent(s) a hydrogen or halogen atom, a —CN or —NO$_2$ group, a $C_3$ to $C_6$ cyclic, or $C_1$ to $C_6$ linear or branched, saturated or unsaturated hydrocarbon group, this hydrocarbon group optionally containing one or more oxygen, nitrogen or sulphur atoms, or else an aryl or heteroaryl group having a 5- or 6-membered ring; and measuring a modification of the optical property of the material and correlating the measured modification to the presence of the halogenated gaseous compound in the medium.

24. The method of claim 23, wherein the halogenated gaseous compound is a halogenated boron complex.

25. The method of claim 24, wherein the halogenated boron complex is BF$_3$ or BCl$_3$.

* * * * *